(12) United States Patent
Yoshikawa et al.

(10) Patent No.: US 6,822,129 B1
(45) Date of Patent: Nov. 23, 2004

(54) METHOD OF CONVERTING AROMATIC COMPOUND

(75) Inventors: Masahito Yoshikawa, Nagoya (JP); Hajime Kato, Nagoya (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/601,414

(22) PCT Filed: Nov. 30, 1999

(86) PCT No.: PCT/JP99/06692

§ 371 (c)(1),
(2), (4) Date: Aug. 1, 2000

(87) PCT Pub. No.: WO00/32547

PCT Pub. Date: Jun. 8, 2000

(30) Foreign Application Priority Data

Dec. 3, 1998 (JP) ............................................ 10-344052

(51) Int. Cl.[7] ................................................ C07C 5/22
(52) U.S. Cl. ...................... 585/481; 585/446; 585/467; 585/470; 585/436; 570/190
(58) Field of Search ................................ 585/446, 467, 585/470, 481, 436, 475; 570/190

(56) References Cited

U.S. PATENT DOCUMENTS

| | | | | |
|---|---|---|---|---|
| 5,215,648 A | * | 6/1993 | Zones et al. | 208/46 |
| 6,043,179 A | * | 3/2000 | Davis et al. | 502/64 |
| 6,103,215 A | * | 8/2000 | Zones et al. | 423/702 |

FOREIGN PATENT DOCUMENTS

| | | | | |
|---|---|---|---|---|
| JP | 60-69042 A | * | 4/1985 | |
| JP | 61-74647 A | * | 4/1986 | |
| JP | 4-103545 A | * | 4/1992 | |
| JP | 4-187649 A | * | 7/1992 | |
| JP | 6-1728 A | * | 1/1994 | |
| WO | WO-91/11258 A1 | * | 8/1991 | |
| WO | WO-97/46986 A2 | * | 12/1997 | |

OTHER PUBLICATIONS

Raul F. Lobo et al., "A Model for the Structure of the Large–Pore Zeolite SSZ–31", J. Am. Chem. Soc., 119, 3732–3744.*
Raul F. Lobo et al., "Characterization of the Extra–Large–Pore Zeolite UTD–1", 1997, J. Am. Chem. Soc., 119, 8474–8484.*
Masahito Yoshikawa et al., "Synthesis, Characterization, and Structure Solution of CIT–5, a New, High–Silica, Extra–Large–Pore Molecular Sieve", 1998, J. Phys. Chem., 102, 7139–7147.*

* cited by examiner

Primary Examiner—Walter D. Griffin
(74) Attorney, Agent, or Firm—Piper Rudnick LLP

(57) ABSTRACT

A method for isomerizing aromatic compounds, wherein at least one aromatic compound is contacted with a zeolite-containing catalyst, and in which the zeolite is characterized in that:

(1) the minimum value of the pore aperture diameter of the major channels therein is larger than 0.65 nanometers, orthe maximum value thereof is larger than 0.70 nanometers, and (2) the major channels do not intersect any others with larger apertures than oxygen 10-membered ring;

and the aromatic compounds are at least one selected from;

(a) aromatic compounds having at least three substituents, (b) aromatic compounds having two substituents of which at least one is a halogen or has at least 2 carbon atoms, and (c) naphthalene or anthracene derivatives having substituent(s), wherein aromatic compounds having a relatively large molecular size can be efficiently isomerized.

12 Claims, 1 Drawing Sheet

METHOD OF CONVERTING AROMATIC COMPOUND

TECHNICAL FIELD

The present invention relates to a method for converting aromatic compounds having substituent(s) and having a relatively large molecular size.

BACKGROUND ART

As known, zeolite is used as a catalyst for conversion of aromatic compounds having substituent(s), for example, for xylene isomerization, toluene disproportionation, etc. It is known that zeolite, especially mordenite-type zeolite is used for conversion of aromatic compounds having at least 3 substituents (Japanese Patent Laid-Open No. 14430/1983).

Zeolite is a porous crystal of which the pores are uniform and have a molecular-level size. It can be a catalyst having good activity and selectivity for conversion of aromatic compounds having a relatively small molecular size, for example, for xylene isomerization, toluene disproportionation or the like, and is so used in some industrial-scale plants. However, for conversion of large-size molecules, using zeolite is often problematic in that the reactant molecules could not penetrate into the zeolite pores, or even if having penetrated thereinto, they could not diffuse rapidly through the pores to receive satisfactory conversion activity. On the other hand, among many kinds of zeolite, pentacyl-type zeolite, mordenite-type zeolite, β-type zeolite, and faujasite-type zeolite are widely used.

β-type zeolite and faujasite-type zeolite have pore apertures with the largest size of these zeolites. However, they have channels with large-size aperture and also have very large spaces formed by intersecting channels. Therefore, their drawback is that some undesired molecules (high-boiling-point compounds) are formed in the intersections of the channels with large space, and the undesired molecules thus formed therein clogs the pores to cause activity depression.

Being different from these catalysts, mordenite-type zeolite has no intersection of large-pore channels, and few undesired large-size molecules can be formed therein. But the aperture size of the pores therein is not so large and it is not so effective for converting large-size molecules. Accordingly, the object of the present invention is to solve the prior art problems, precisely to provide a highly-active, selective and long-life method for converting aromatic compounds having a large molecular size, concretely, for converting at least one aromatic compound selected from (a) aromatic compounds having at least three substituents, (b) aromatic compounds having two substituents of which at least one is a halogen or has at least 2 carbon atoms, and (c) naphthalene or anthracene derivatives having substituent(s).

DISCLOSURE OF THE INVENTION

To attain the subject matter as above, the method of the invention principally comprises contacting at least one aromatic compound with a zeolite-containing catalyst, wherein the zeolite is characterized in that;

(1) the minimum value of the pore aperture diameter of the major channels therein is larger than 0.65 nanometers (hereinafter referred to as nm), or the maximum value thereof is larger than 0.70 nm, and (2) the major channels do not intersect any others with larger apertures than an oxygen 10-membered ring;

and the aromatic compounds are at least one compound selected from the group consisting of;

(a) aromatic compounds having at least three substituents, (b) aromatic compounds having two substituents of which at least one is a halogen or has at least 2 carbon atoms, and (c) naphthalene or anthracene derivatives having substituent(s).

BEST MODES OF CARRYING OUT THE INVENTION

Figure 1:
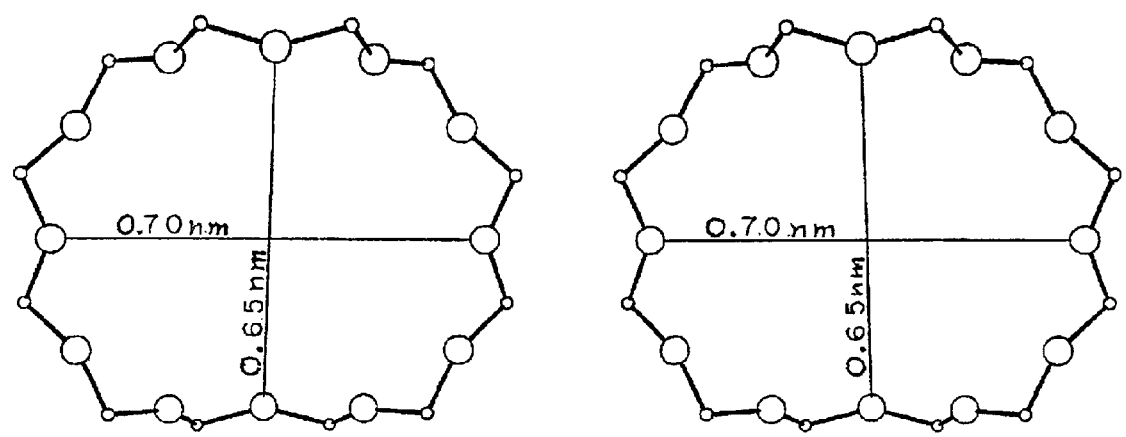
FIG. 1 is a stereoscopic view showing the pore aperture of major channels of mordenite-type zeolite.

The invention is described in detail hereinunder. Zeolite referred to herein is a crystalline microporous material which has the channels with uniform and molecular-level size pores, including crystalline aluminosilicate, crystalline metallosilicate, crystalline metalloaluminosilicate, crystalline aluminophosphate, crystalline metalloaluminophosphate, and crystalline silicoaluminophosphate. The metallosilicate and metalloaluminosilicate referred to herein are aluminosilicate derivatives in which aluminium is partly or entirely substituted with any other metals except aluminium, such as gallium, iron, titanium, boron, cobalt, chromium, etc. Similarly, metalloaluminophosphate indicates aluminophosphate derivatives in which aluminum or phosphorous is partly substituted with any other metals except itself.

Zeolite for use in the invention is not specifically defined for its composition, for which various compositions such as those mentioned above are adopted. However, its structure is indispensably defined as follows:

(1) the minimum value of the pore aperture diameter of the major channels therein is larger than 0.65 nm, or the maximum value thereof is larger than 0.70 nm, and (2) the major channels do not intersect any others with larger apertures than an oxygen 10-membered ring.

In other words, the zeolite for use in the invention must satisfy the two requirements (1) and (2).

The major channels of the zeolite referred to herein are meant to indicate the channels having the largest pore apertures in one zeolite structure. The pore size in zeolite, in general, is represented by reference to an oxygen n-membered ring in which n indicates the number of oxygen atoms that constitute the pore aperture. For satisfying the requirement (1), the aperture size of the pores or channels must be at least equal to or larger than that of an oxygen 12-membered ring. Zeolite having channels of which the pore aperture size is larger than that of an oxygen 12-membered ring satisfies the requirement (1), but some others having the same do not. For example, mordenite-type zeolite, though having oxygen 12-membered ring pores (channels), does not satisfy the requirement (1), since the minimum value of the pore opening diameter of the pores therein is 0.65 nm and the maximum value thereof is 0.70 nm. On the other hand, SSZ-31 of which the structure has been recently clarified (R. F. Lobo et al.; J. Am. Chem. Soc., Vol. 119, pp. 3732–3744, 1997) satisfies the requirement (1), since the maximum value of the pore opening diameter of the pores therein is 0.86 nm and the minimum value thereof is 0.57 nm. Zeolite having oxygen 12-membered ring pores and satisfying the requirement (1) in regard to the pore aperture diameter, and zeolite having pores larger than 12-membered ring pores in regard to the pore aperture diameter, for example, zeolite having 14-membered ring pores are within the scope of zeolites for use in the invention.

Any one can know the sizes of pore apertures in zeolite of which the structure is known. Various types of zeolites of which the structure has been clarified, and the atomic configuration in such known different types of zeolites are described in Atlas of Zeolite Structure Types (W. M. Meier, D. H. Olson, Ch. Baerlocher, Zeolites, 17(½), 1996; Reference 1). In the section of Channels in Reference 1, they show the crystallographic free diameter. The free diameter values are based on any oxygen radius of 0.135 nm. In this shape, both the maximum value and the minimum value are shown for a noncircular aperture. In this reference, the pore aperture is stereoscopically drawn as FIG. 1, and both its maximum value and the minimum value are given therein, The maximum value and the minimum value of the pore aperture referred to in the invention is just the values shown in the reference. For all types of zeolites clarified in Reference 1, their data of aperture size given in Reference 1 are referred to herein, irrespective of their composition, for judging their applicability to the invention (in fact, however, the pore size will vary, depending on the composition and the ambient temperature). For the others not shown in Reference 1 but disclosed in any other references such as journals and the like, their applicability to the invention is determined from the pore aperture diameter from their structure disclosed in such other references.

For the types of zeolite not clarified in Reference 1 in reference to their pore aperture diameter, the maximum value and the minimum value of the pore aperture therein shall be determined in a simplified method such as that mentioned below. Based on the atomic configuration and the space group of zeolites shown in references, a crystal model is constructed. For this, the atomic configuration and the space group are preferably subject to a Rietveld refinement. The oxygen atoms constituting the pore aperture are combined with each other via a diagonal line drawn therebetween, and the maximum interatomic distance and the minimum interatomic distance are obtained (for this, the size of the oxygen atom itself is neglected, and the interatomic distance is obtained from the positional difference between the connected two oxygen atoms). From the maximum or minimum interatomic distance thus obtained, 0.27 nm (the diameter of one oxygen atom) is subtracted to give the maximum or minimum value of the pore opening size.

Zeolite having a larger pore aperture is more preferred for use in the invention, as having a higher conversion activity and ensuring a higher reaction yield. Therefore, it is desirable that both the minimum value and the maximum value of the pore opening diameter of the pores in zeolite for use herein are larger than 0.70 nm. For the pore entrance of the major pores in zeolite for use herein, larger pores than oxygen 12-membered ring pores are preferred to oxygen 12-membered ring pores. Though it is not clear, the reason may be because molecules could diffuse more rapidly in larger pores in the zeolite. If molecules diffuse slowly in pores in zeolite, their reaction will be retarded, or that is, the reaction activity in the pore of such zeolite is poor. In addition, if molecules diffuse slowly in pores in zeolite, the time for which they are contacted with zeolite shall be prolonged, thereby often inducing side reactions such as decomposition, and the reaction yield is lowered. Accordingly, enlarging the pore diameter in zeolite to promote the diffusion of molecules through the pores therein increases the conversion activity and the reaction yield. The uppermost limit of the pore diameter is not specifically defined, for which, however, it is desirable that the maximum value of the pore entrance diameter is at most 1.1 nm, more preferably at most 0.9 nm. Though it is not clear, the reason may be because too large pores, if any in the zeolite, will provide a site for large molecules to be formed therein, and high-boiling-point substances thus formed therein will clog the pores to shorten the catalyst life of the zeolite.

Zeolite for use in the invention must satisfy not only the requirement (1) indicating that the minimum value of the pore aperture diameter of the major channels therein is larger than 0.65 nm, or the maximum value thereof is larger than 0.70 nm, but also the requirement (2) indicating that the major channels do not intersect with any others that have larger apertures than oxygen 10-membered ring pores.

For its pore structure, zeolites have one-dimensional pore systems or poly-dimensional pore systems. Preferably, zeolite for use in the invention has essentially one-dimensional pores. The pore structure of the one-dimensional pore system is generally such that the major channels do not intersect with any other channels having pore sizes not smaller than oxygen 7-membered pores. Being different from it, the pore structure of poly-dimensional pores is such that some major channels intersect some other channels with apertures that are not smaller than oxygen 7-membered ring pores. The invention is directed to conversion of aromatic compounds having a large molecular size, as will be described hereinunder, in which, therefore, zeolites having small pores that are not larger than oxygen 10-membered ring pores are substantially useless, since the pores therein are too small to be effective to perform the intended conversion. Accordingly, in the invention, it is recognized that the pore structures of zeolites in which the major channels intersect the other pores not larger than oxygen 10-membered ring pores are substantially one-dimensional, and zeolites of the type having such a one-dimensional pore structure are within the scope of zeolites for use in the invention. On the other hand, zeolite in which large channels intersect with each other, for example, β-type zeolite in which oxygen 12-membered ring pores intersect with each other shall have an extremely large space around the intersecting points, and undesirable reactions yielding high-molecular-weight substances will be inevitable in such a large space. The high-molecular-weight substances thus formed in the large space will clog the pores, whereby the activity of the zeolite will be lowered. This is the reason why one-dimensional pore-structured zeolites are preferred for use in the invention. Zeolite in which some major channels intersect some other channels having not larger apertures than oxygen 10-membered ring will have substantially no other open pores expect the major channels, and this type of zeolite is adopted in accordance with the invention without problem. Preferably, however, in zeolite for use in the invention, the channels that may intersect the major channels do not have larger pores than an oxygen 10-membered ring.

The structure of zeolite for use in the invention is not specifically defined provided that it satisfies the requirements defined herein. With reference to the structural code of three letters indicated in Atlas of Zeolite Structure Types (W. M. Meier, D. H. Olson, Ch. Baerlocher, Zeolites, 17(½), 1996), concretely, the structure of zeolite for use in the invention include VFI, AET, AFI, AFR, AFS, ATS, BOG, BPH, DFO, GME, LTL, MAZ, MEI, OFF. In addition, it further includes CFI having large pores of which the pore entrance diameter is larger than that of oxygen 12-membered ring pores (M. Yoshikawa et al., Journal of Physical Chemistry, B, Vol. 102, pp. 7139–7147), and UTD-1 (R. F. Lobo et al., Journal of American Chemical Society, Vol. 119, pp. 8474–8484, 1997). Further, SSZ-31 mentioned above is also within the scope of zeolite for use in the invention. Of those, preferred for use herein are AFI, GME, LTL, MAZ, MEI, OFF, CFI, UTD-1, and SSZ-31; more preferred are CFI and UTD-1; even more preferred is CIT-5 zeolite. The structure type code of this zeolite is CFI.

Those types of zeolites may be natural ones or synthetic ones. Preferred is synthetic zeolite, as its composition can be controlled in any desired manner. Any known method can be adopted for producing it. For zeolite of which the structure is not clarified as yet, it will be impossible to identify the pore aperture diameter. If such large crystals of zeolite are prepared, the structure of the zeolite may be determined according to an M. Yoshikawa et al's method (Journal of Physical Chemistry, B, Vol. 102, pp. 7139–7147, 1998) or to a C. C. Freyhardt et al's method (Journal of American Chemical Society, Vol. 118, pp. 7299–7310, 1996).

Specific examples of zeolite structures for use in the invention are mentioned hereinabove, and the composition of zeolite can be selected with reference to the intended reaction. For acid catalyst reaction, preferably used is any or crystalline aluminosilicate, trivalent metal-containing crystalline metallosilicate, and crystalline silicoaluminophophate; more preferred are crystalline aluminosilicate and crystalline gallosilicate; and even more preferred is crystalline aluminosilicate. In crystalline aluminosilicate and metallosilicate for use in the invention, the ratio (by mol) of Si/(trivalent metal) is not specifically defined, but preferably falls between 5 and 500, more preferably between 5 and 200, even more preferably between 7 and 100. Zeolite having a smaller ratio of Si/(trivalent metal) will have a larger number of active sites, and is therefore preferred for use in the invention. On the other hand, zeolite having a larger ratio of Si/(trivalent metal) will be more hydrophobic, and is therefore preferred for conversion of organic compounds, since it can more easily absorb the reaction substrate. Zeolite having a well-balanced ratio of Si/(trivalent metal) in consideration of these facts may be suitably selected for use in the invention. For oxidation with hydrogen peroxide, preferred is crystalline titanosilicate. For hydroxylation with nitrogen suboxide, preferred is crystalline ferrosilcate.

In case the zeolite for use in the invention has ion-exchanging sites, the sites may be ion-exchanged with any other different ions. In case the zeolite is used herein as an acid catalyst, in general, it is previously subjected to a few times of ion exchange treatment with an aqueous solution of an ammonium salt and then calcined to be an acid-type zeolite catalyst.

The catalyst of zeolite for use in the invention has a substantially one-dimensional pore system. If the zeolite crystals constituting it are too large, smooth adsorption of reaction substrates thereto and smooth release of products therefrom will be difficult, and the reaction activity on the zeolite catalyst will be poor. Accordingly, zeolite for use in the invention is preferably composed of small crystals. Concretely, the crystal size is at most 1 $\mu$m, more preferably at most 0.5 $\mu$m, even more preferably at most 0.1 $\mu$m. The crystal size can be determined through scanning electromicroscopy (SEM) or transmission electromicroscopy (TEM).

For preferable use in the invention, the zeoite is formed. Zeolite alone may be formed, or may be granulated along with a binder such as alumina, clay, etc. For granulating it, for example, the zeolite is kneaded with a binder such as alumina or the like, then extruded out through an extruder, and rounded into granules by the use of an equipment like Marumerizer (a type of granulator, pelletizer or the like).

From the zeolite-containing catalyst, in general, crystal water existing therein and organinc substances used in producing it and still remaining therein are removed before use. In general, it may be heated at 200 to 600° C., whereby crystal water and the organic substances can be almost completely removed from zeolite.

The catalyst may contain metal. Or example, it is desirable to prolong the catalyst life that the acid catalyst contains a noble mental, and the reaction is carried out in the presence of hydrogen. Though not clear, the reason may be because the catalyst could more readily receive protons and it could be prevented from coking. The noble metal that may be in the catalyst is not specifically defined, but rheniuhm is the best. The reason is because the catalyst containing rehenium will hardly undergo hydrogenolysis.

The invention is a method for converting aromatic compounds, comprising contacting the zeolite-containing catalyst mentioned above with at least one aromatic compound selected from:

(a) aromatic compounds having at least three substituents, (b) aromatic compounds having two substituents of which at least one is a halogen or has at least 2 carbon atoms, and (c) naphthalene or anthracene derivatives having substituent(s).

The aromatic compounds in the invention are limited to those having a relatively large molecular size. For converting compounds having a small molecular size, such as xylene, toluene and others, conventional pentacyl-type zeolite (MFI) and mordenite-type zeolite (MOR) will give enough reaction property but they do not give enough reaction property for converting aromatic compounds having a large molecular size. The method of the invention is directed to the efficient conversion of such aromatic compounds having a relatively large molecular size. Aromatic compounds having a relatively large molecular size in the invention are at least one selected from:

(a) aromatic compounds having at least three substituents, (b) aromatic compounds having two substituents of which at least one is a halogen or has at least 2 carbon atoms, and (c) naphthalene or anthracene derivatives having substituent(s).

The aromatic compounds (a) having at least three substituents are those having at least three substituents except hydrogen on the benzene ring. The type of the substituents is not specifically defined, including, for example, halogens, hydrocarbons, hydroxyl groups, oxygen-containing hydrocarbons, halogen-containing hydrocarbons, nitrogen-containing substituents, etc. For example, the aromatic compounds include trimethylbenzene, tetramethylbenzene, chloroxylene, dichloroxylene, dichlorotoluene, trichlorotoluene, dichloroaniline, xylenol, trimethylphenol, dimethylbenzoic acid, etc. Needless-to-say, these are not limitative. The invention is especially effective to the compounds having at least one halogen substituent. The invention is more effective to the compounds having a larger number of halogen substituents.

The aromatic compounds (b) having two substituents of which at least one is a halogen or has at least 2 carbon atoms are meant to indicate those having at least one bulky substituent. For example, they include chlorotoluene, bromotoluene, ethyltoluene, propyltoluene, diethylbenzene, butyltoluene, chloroethylbenzene, chloropropylbenzene, bromoethylbenzene, bromopropylbenzene, phenoxybenztoluene, etc. Needless-to-say, these are not limitative.

The naphthalene or anthracene derivatives (c) having substituent(s) are naphthalene or anthracene compounds having substituent(s) except hydrogen. For example, they include methylnaphthalene, propylnaphthalene, dimethylnaphthalene, halogenonaphthalenes, etc. Needless-to-say, these are not limitative.

The invention is especially effective for converting aromatic compounds having halogen substituent(s). The reason will be because the zeolite catalyst for use in the invention has large pores through which, therefore, such bulky aromatic compounds could easily diffuse without undergoing possible dehalogenation.

The invention is a method for converting aromatic compounds, which is characterized in that the specific catalyst is contacted with aromatic compounds such as those mentioned above. In the invention, however, the type of conversion is not specifically defined, including, for example, isomerization, disproportionation, transalkylation, alkylation, oxidation, hydroxylation, acylation, reduction, etc. The invention is specially effective for isomerization, disproportionation, and transalkylation. The reason will be because bulky substituents shall move in zeolite pores for isomerization, and because reaction intermediates with two molecules bonded will be formed in disproportionation and transalkylation. For these types of conversion, therefore, the invention will be especially effective as zeolite having large pores is used therein. Above all, isomerization of bulky molecules must be attained without disproportionation. for which, therefore, zeolite having substantially one-dimensional large pores is especially effective. For example, isomerization of dichlorotoluene has been already industrialized, for which, however, conventional catalyst are unsatisfactory in point of activity, selectivity and life. According to the method of the invention, the capability of conversion per one active site in the catalyst used is high. In addition, since the catalyst used does not have any large space in the pores therein, a reaction into polymers having a high molecular weight, such as dimerization, trimerization and others, is prevented therein. Further, the compounds could rapidly diffuse through the pores in the catalyst used, and the time for contacting the compounds with the catalyst may be shortened to prevent some side reactions such as decomposition, etc. To that effect, the invention is especially effective for isomerization of tri-substituted compounds, but is not limited thereto.

The method of the invention is especially effective for isomerization of aromatic compounds having at least three substituents, such as dihalogenotoluenes, trihalogenobenzenes, trialkylbenzenes, etc. Concretely, it is effective for isomerization of dichlorotoluene, isomerization of trichlorobenzene, and isomerization of trimethylbenzene.

The invention also encompasses a case in which aromatic compounds such as those mentioned above are not in the reaction substrate but are formed in situ through a reaction process, and the thus-formed compounds are converted into intended products. For example, in a process where naphthalene is methylated to give dimethylnaphthalene, methylnaphthalene formed in situ is converted into the product. Therefore, the type of the process is within the scope of the invention.

The method of conversion for the invention is not also specifically defined. Any of liquid-phase reaction and vapor-phase reaction is adopted herein. The reaction pressure and the reaction temperature for the invention are not also specifically defined, as varying depending on the type of conversion. Any of fixed bed, mobile bed and fluidized bed systems are adopted herein. As being easy to operate on an industrial scale, a flow method with a fixed bed is especially preferred for the invention. For preventing the catalyst from coking, hydrogen may be present in the reaction system.

EXAMPLES

The invention is described hereinunder with reference to its examples.

(Production of CIT-5)

An aqueous solution of N(16)-methylsparteinium hydroxide (hereinafter referred to as MeSPAOH) was prepared as follows: 127 g of (–)-spartteine sulphate pentahydrate (from Aldrich) was dissolved in 190 g of aqueous 10% NaOH solution with stirring, then extracted three times with 200 ml of toluene, washed once with 200 ml of a saturated saline solution, dewatered with potassium carbonate, and thereafter evaporated by the use of a rotary evaporator remove toluene. The dry product was recovered with 500 ml of acetone, to which was gradually added 127.7 g of methyl iodide with stirring to give a white crystal deposit. This was washed with diethyl ether, and then dried. This was dissolved in isopropanol and recrystallized, then washed with a ½ solution of isopropanol/ethyl acetate and dried. The resulting product was identified as N(16)-methylsparteiniumiodide by its $^1$H-NMR and $^{13}$C-NMR. Next, the iodide was dissolved in water and applied to an anion exchange resin (OH type), through which it was converted into a hydroxide. The resulting hydroxide was concentrated by the use of a rotary evaporator.

Ludox HS-30 (from DuPont) was used as a silica source; aluminium nitrate 9-hydrate (from Nakarai Tesq) was used as an aluminium source; and anhydrous lithium hydroxide (from Kishida Chemical) was used as a lithimn source. From these, prepared was a mixture having a compositional formula, $SiO_2$:0.1LiOH:0.2MeSPAOH:0.01Al($NO_3$)$_3$:40$H_2O$ (by mol).

The mixture was stirred for 2 hours, and then heated in a Teflon lined autoclave at 175° C. for 9 days. The resulting zeolite was taken out through filtration, washed with water, dried at 100° C. and analysed through X-ray diffractiometry, by which it was identified as CIT-5. According to the reference (M. Yoshikawa et al's Journal of Physical Chemicatry, B, Vol. 102, pp. 7139–7147, 1998), the zeolite CIT-5 contains oxygen 14-membered ring pores, and the aperture is nearly circular and has a diameter of about 0.73 nm. In this, the major channels do not intersect any other pores.

(Preparation of Catalyst)

The dry product CIT-5 was tabletted into tablets. These were calcined at 550° C. for 2 hours, then cooled and crushed, from which was obtained a 12 to 60-mesh granule fraction. To 5 g of the granule fraction, added was 30 g of an aqueous 10 wt. % ammonium chloride solution, and heated at 80° C. for 1 hour. This was dewatered through decantation, and then washed with 30 g of water. This treatment was repeated four times. Finally, this was fully washed with water at 80° C.

(Preparation of Comparative Catalysts)

Toso's mordenite (silica/alumina=20 (by mol); the pore aperture of the major channels in this has a size of 0.65 (the minimum value)×0.70 (the maximum value) nm, and the major channels intersects the other oxygen 8-membered pores therein to give a substantially one-dimensional pore structure system—Reference 1), and PQ Corporation's acid-type β-type (β-H) zeolite (silica/alumina=23 (by mol); the pore aperture of the major channels in this has a size of 0.76×0.64 nm, and the major channels intersect the other oxygen 12-membered ring channels therein—Reference 1)

were processed in the same manner as above to prepare comparative catalysts. As containing no organic substance, the formed products were not baked.

(Reaction)

Each catalyst was calcined at 550° C. for 2 hours, and then cooled in a desiccator filled with diphosphorus pentoxide. 3 g of 2,4-dichlorotoluene (2,4-DCT) was put into a 5-ml stainless autoclave, to which was added 1 g of the catalyst having been cooled in the desiccator, and sealed. This was kept heated in an oven at 330° C. for 3 hours. After cooled, the resulting product was analyzed through gas chromatography.

(Results)

The relative ratio of 2,4-DCT conversion per one active site of the catalyst used was as follows: The number of the active sites in each catalyst was determined from the amount of aluminum in zeolite. The degree of conversion was determined from the weight loss of 2,4-DCT before and after the reaction.

CIT-5:mordenite:$\beta$=2.3:1:1.8

The relative ratio of the amount of high-boiling-point products formed was as follows: The high-boiling-point products are those having a larger molecular weight than dichloroxylene.

CIT-5:mordenite:$\beta$=1:3:4

From the data, it is understood that the CIT-5 catalyst attained a higher degree of 2,4-DCT conversion than the others, mordenite and $\beta$-zeolite, and the amount of the high-boiling-point products formed by the use of the CIT-5 catalyst is smaller than that formed by the use of the other catalysts.

Industrial Applicability

According to the invention, aromatic compounds having substituent(s) and having a relatively large molecular size can be efficiently converted, and the invention is applicable to various chemical industries.

What is claimed is:

1. A method for isomerizing aromatic compounds, which comprises contacting at least one aromatic compound with a zeolite-containing catalyst having a pore structure of controlled diameter, said zeolite being characterized in that:
   (1) when said pore aperture has a circular or a non-circular cross section and accordingly has a minimum diameter and a maximum diameter, the minimum value of the pore aperture diameter of the major channels therein is larger than 0.65 nanometers, and the maximum value thereof is larger than 0.70 nanometers,
   (2) said major channels do not intersect any others having larger apertures than an oxygen 10-membered ring, and
   (3) said zeolite has a crystal size of at most 1 $\mu$m;
and wherein said aromatic compounds are selected from the group consisting of:
   (a) aromatic compounds having at least three substituents,
   (b) aromatic compounds having two substituents of which at least one is a halogen or has at least 2 carbon atoms, and
   (c) naphthalene or anthracene derivatives having substituent(s).

2. The method for isomerizing aromatic compounds as claimed in claim 1, wherein said minimum value of the pore aperture diameter of said major channels in the zeolite is 0.7 nanometers or above.

3. The method for isomerizing aromatic compounds as claimed in claim 1 or 2, wherein the pore aperture size of said major channels in the zeolite is larger than an oxygen 12-membered ring.

4. The method for isomerizing aromatic compounds as claimed in claim 1 or 2, wherein the catalyst is contacted with a substituted aromatic compound in which at least one substituent is a halogen.

5. The method for isomerizing aromatic compounds as claimed in claim 1 or 2, wherein the catalyst is contacted with an aromatic compound having at least three substituents.

6. The method according to claim 1, wherein said zeolite is one selected from the group consisting of SSZ-31, VFI, AET, AFI, AFR, AFS, ATS, BOG, BPH, DFO, GME, LTL, MAZ, MEI, OFF, CFI having large pores of which the pore entrance diameter is larger than an oxygen 12-membered ring pore, and UTD-1.

7. The method according to claim 1, wherein the maximum value of the pore entrance diameter is at most 1.1 nm.

8. The method according to claim 1, wherein said zeolite has a one-dimensional pore system.

9. The method according to claim 1, wherein said zeolite is synthetic.

10. The method according to claim 1, wherein said zeolite is formed.

11. The method according to claim 1, wherein said catalyst contains metal.

12. A method for isomerizing aromatic compounds, which comprises contacting at least one aromatic compound with a zeolite-containing catalyst having a pore structure of controlled diameter, said zeolite being characterized in that:
   (1) when said pore aperture has a circular or a non-circular cross section and a minimum diameter and a maximum diameter, the minimum value of the pore aperture diameter of the major channels therein is larger than 0.65 nanometers, and the maximum value thereof is between 0.70 and 0.9 nanometers,
   (2) said major channels do not intersect any others having larger apertures than an oxygen 10-membered ring, and
   (3) said zeolite has a crystal size of at most 1 $\mu$m;
and wherein said aromatic compounds are selected from the group consisting of:
   (a) aromatic compounds having at least three substituents,
   (b) aromatic compounds having two substituents of which at least one is a halogen or has at least 2 carbon atoms, and
   (c) naphthalene or anthracene derivatives having substituent(s).

* * * * *

UNITED STATES PATENT AND TRADEMARK OFFICE
CERTIFICATE OF CORRECTION

PATENT NO. : 6,822,129 B1
DATED : November 23, 2004
INVENTOR(S) : Yoshikawa et al.

It is certified that error appears in the above-identified patent and that said Letters Patent is hereby corrected as shown below:

Title page,
Item [57], ABSTRACT,
Line 7, please change "orthe" to -- or the -- before "maximum".

Column 3,
Line 52, please change "ofthe" to -- of the -- before "pore".

Column 6,
Line 7, before "example", please change "Or" to -- For --;
Line 13, please change "rheniuhm" to -- rhenium --;
Line 14, please change "rehenium" to -- rhenium --.

Column 9,
Line 45, please delete "accordingly has";
Line 50, after "(2)", please insert -- the pore structure has essentially one dimensional pores wherein --.

Column 10,
Line 22, please change "MEJ" to -- MEI --.

Signed and Sealed this

Fifth Day of April, 2005

JON W. DUDAS
*Director of the United States Patent and Trademark Office*